Nov. 30, 1948. E. S. BOERNER Plant Pat. 811
ROSE PLANT
Filed May 6, 1947
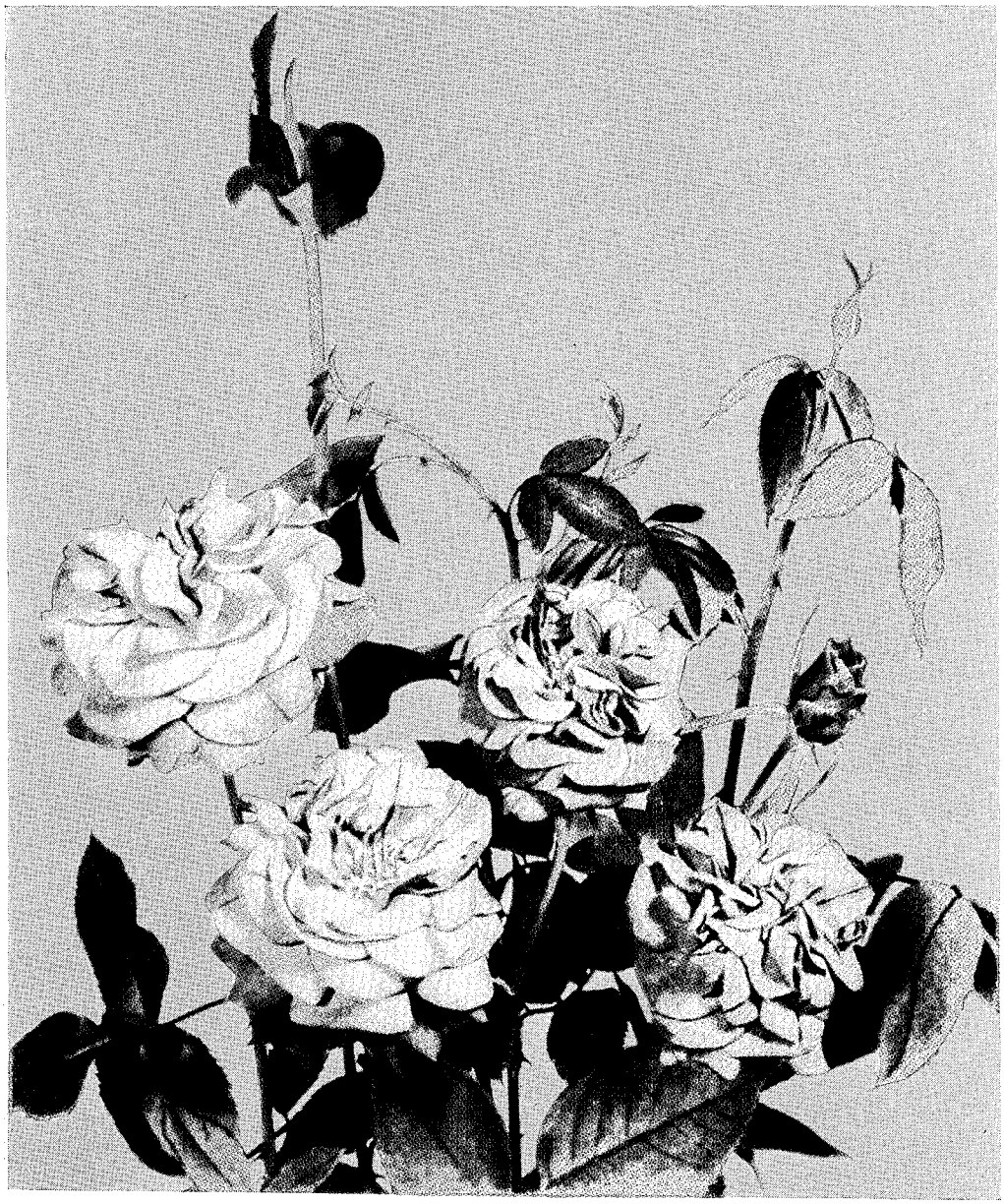
Inventor
E. S. Boerner
By Robbs & Robb
Attorneys Patented Nov. 30, 1948

Plant Pat. 811

UNITED STATES PATENT OFFICE

811

ROSE PLANT

Eugene S. Boerner, Newark, N. Y., assignor to Jackson & Perkins Company, Newark, N. Y., a corporation of New York Application May 6, 1947, Serial No. 746,231

1 Claim. (Cl. 47—61)

The present invention relates to a new and distinct variety of rose plant of the large flowered polyantha class, resulting from crossing the varieties "Crimson Glory" and an unnamed seedling (Orange Floribunda).

This new variety is distinguished from its parents and other known roses in the following respects:

(1) The color of the flowers which is new and unusual in the rose field.

(2) The camellia-like shape and large size flowers.

(3) The great number of petals and their uncrowded arrangement which close the center.

(4) The unusual, strong, sweet Rose geranium foliage fragrance.

(5) The different and distinctive foliage specifically described hereinafter.

(6) The color of the buds which open an Oxblood Red and finish as Spectrum Red flowers.

Asexual reproduction of this new variety shows the foregoing characteristics come true to form and are established.

In the drawing is shown a group of specimens of the flowers and foliage at different stages of development and depicting the distinctive coloring of both.

The following is a detailed description of the new variety, color terminology being in accordance with Ridgway's Color Standard:

Parentage: Seedling.

*Seed parent.*—"Crimson Glory" (Pl. Pat. No. 105).

*Pollen parent.*—Unnamed Orange Floribunda seedling (unpatented).

Classification:

*Botanic.*—Large flowered polyantha.

*Commercial.*—Floribunda.

*Flower*

(Observations made in the greenhouses of Jackson & Perkins Company, Newark, New York, in the month of March.)

Blooming habit: Recurrent—continuous.

Bud:

*Size.*—Medium.

*Form.*—Urn. Is not affected by wet or hot weather.

*Color.*—When sepals first divide—Victoria Lake, Plate 1; when petals begin to unfurl—Oxblood Red, Plate 1; When half blown—inside of petals, Oxblood red, Plate 1, shaded with Carmine, Plate 1; reverse of petals, Carmine, Plate 1, overcast with Oxblood Red, Plate 1.

*Sepals.*—Serrated, branched, "hood" above bud. Curl back when petals begin to unfurl. Color—inside—Absinthe Green, Plate 31; outside—Forest Green, Plate 17.

*Calyx.*—Shape—pear. Size—small. Aspect—smooth. Odor when rubbed—None. Color—Lettuce Green, Plate 5.

*Peduncle.*—Length—short. Aspect—prickly. Color—Oil Green, Plate 5. Strength—bending; slender.

*Opening.*—Bud opens up well. Is not affected by adverse weather conditions.

Bloom:

*Size.*—Medium. Average size when fully expanded, 4''.

*Borne.*—Singly, several together.

*Stems.*—Medium length, normal stems.

*Form.*—When first open—flat. Permanence—flattens and reflexes some.

*Petalage.*—Very double (many petals and stamens hidden). Number of petals under normal conditions, 40 to 50.

*Color.*—Center of flower—Carmine, Plate 1. Outer petals—Carmine, Plate 1, overlaid with Spectrum Red, Plate 1. Base of petals (aiglet)—Massicot Yellow, Plate 16. Inside of petals—Spectrum Red, Plate 1, overlaid with Scarlet Red, Plate 1. Reverse of petals—Pomegranate Purple, Plate 12, overcast with Rose Red, Plate 12. General tonality from a distance—Spectrum Red, Plate 1.

*Discoloration.*—General tonality at end of first day—Carmine, Plate 1, overlaid with Scarlet Red, Plate 1. Second day—Carmine, Plate 1, overlaid with Scarlet Red, Plate 1. Third day—Scarlet Red, Plate 1, overlaid with Scarlet, Plate 1.

Petals:

*Texture.*—Thin. Is not affected by wet or hot weather.

*Appearance.*—Inside—shiny; outside—satiny.

*Form.*—Oval, pointed.

*Arrangement.*—Imbricated (regularly arranged shingle-like). Petaloids in center—few; small.

*Persistence.*—Drop off cleanly.

*Fragrance.*—Strong. Nature—that of rose geranium foilage.

*Lasting quality.*—On the plant and as cut flower—long.

Genital organs:

*Stamens.*—*Anthers*—large; many. Color—

Primuline Yellow, Plate 16. Arrangement—regular around styles. *Filaments (threads)*—medium length. Color—Eugenia Red, Plate 13.

*Pollen.*—Mustard Yellow, Plate 16.

*Styles.*—Loosely separated, uneven length; medium length; thin.

*Stigmas.*—Light Chalcedony Yellow, Plate 17.

*Ovaries.*—All enclosed in calyx.

*Plant*

Form: Bush.

Growth: Vigorous; compact.

Foliage: 5 to 7 leaflets or more.

*Size.*—Large.

*Quantity.*—Abundant.

*Color.*—New foliage: upper side—Yellowish Oil Green, Plate 5; serrations—Carmine, Plate 1; under side—Yellowish Oil Green, Plate 5, overcast with Carmine, Plate 1. Old foliage: upper side—Varley's Green, Plate 18; under side—Rainette Green, Plate 31.

*Shape.*—Oval pointed.

*Texture.*—Upper side and under side smooth. Ribs and veins—ordinary.

*Edge.*—Serrated (saw toothed).

*Serration.*—Single; sharp.

*Leaf stem.*—Citrine, Plate 4. Under side—smooth.

*Stipules.*—Short; smooth.

*Disease resistance.*—Resistant.

Wood:

*New wood.*—Color—Yellowish Oil Green, Plate 5. Bark—smooth.

*Old wood.*—Color—Cress Green, Plate 31. Bark—smooth.

Thorns:

*Thorns.*—Quantity—on main stalks from base and on laterals from stalk—ordinary. Form—narrow base; medium length; hooked downward. Color when young—Spectrum Red, Plate 1. Position—irregular.

*Prickles and needles.*—On main stalks and on laterals—none.

I claim:

A new and distinct variety of rose plant of the Floribunda class, characterized as to novelty by the color of the flowers and their change from that in the bud stage to that in the full blown stage, the large size and shape of the flowers, the large number of petals and their arrangement, the strong fragrance of the sweet rose geranium foliage, and the distinctive form and color of the foliage, substantially as shown and described.

EUGENE S. BOERNER.

No references cited.